United States Patent [19]
Yein et al.

[11] Patent Number: 5,863,746
[45] Date of Patent: Jan. 26, 1999

[54] METHOD OF MEASURING BILIRUBIN

[75] Inventors: Fred Shu-Chung Yein, Fullerton; Cecilia Z. Schultz, Garden Grove, both of Calif.

[73] Assignee: Beckman Coulter, Inc., Fullerton, Calif.

[21] Appl. No.: 60,460

[22] Filed: Apr. 15, 1998

Related U.S. Application Data

[62] Division of Ser. No. 628,419, Apr. 5, 1996, Pat. No. 5,783,407.

[51] Int. Cl.$^6$ .................................................. C12Q 1/26
[52] U.S. Cl. ............................. 435/25; 435/10; 435/11; 435/14; 435/810
[58] Field of Search .................. 435/10, 11, 14, 435/25, 28, 810, 962, 975; 436/97; 422/61

[56] References Cited

U.S. PATENT DOCUMENTS

| | | | |
|---|---|---|---|
| 4,554,249 | 11/1985 | Kodaka et al. | 435/10 |
| 4,600,689 | 7/1986 | Matsui et al. | 435/25 |
| 5,705,353 | 1/1998 | Oh et al. | 435/7.92 |

FOREIGN PATENT DOCUMENTS

WO 86/00933  2/1986  WIPO.

*Primary Examiner*—Ralph Gitomer
*Attorney, Agent, or Firm*—William H. May; Margaret A. Kivinski

[57] ABSTRACT

An assay for detecting in a test sample, an analyte that undergoes auto-oxidation is disclosed. The assay comprises the steps of forming a reaction mixture by combining in an aqueous medium (i) a sample containing the analyte and (ii) a stabilizer that reduces the rate of radical mediated auto-oxidation of the analyte. The reaction mixture is incubated for a period of time and the rate of auto-oxidation is detected. When the detected rate of auto-oxidation is substantially zero, a sufficient quantity of an enzyme is added, that catalyzes the oxidation of the analyte. In the presence of the stabilizer, the analyte can be oxidized to a product species. The product species, the analyte, or both can be detected.

13 Claims, 1 Drawing Sheet

METHOD OF MEASURING BILIRUBIN

This application is a divisional of application Ser. No. 08/628,419 filed Apr. 5, 1996 which has issued as U.S. Pat. No. 5,783,407.

BACKGROUND

Diagnostic assays play a significant role in the detection and diagnosis of diseases. The development of diagnostic assay technology has made possible the precise measurement of minute amounts of analyte in samples of serum, plasma, saliva, cerebral spinal fluid, amniotic fluid and urine. Applications of such assays include measuring drug concentrations administered to patients for the treatment of diseases and detecting blood components resulting from diseases including cancer. Thus, their applications in the fields of biology and medicine have made them increasingly important and versatile as diagnostic tools.

There are complications, however, with the uses of assays. The sensitivity and accuracy of these assays are often limited by the instability of the analyte of interest due to the conditions of the assay. Such limitations can make detection and measurement of the analyte of interest unreliable, as well as decrease the sensitivity of the assay.

The effects of these limitations can be disastrous since their presence in assays could cause inaccurate results leading to misdiagnosis and potentially inappropriate treatment.

In certain liver diseases such as hepatitis, liver cirrhosis, or obstructive jaundice, the diconjugate bilirubin species is believed to be elevated in early stages of the disease.

Bilirubin is a typical metabolic product of hemoglobin which is an oxygen carrier in blood. Determination of the amount of bilirubin in body fluid, especially blood, is important for detection of hemolysis and for checking liver function. One symptom of excess bilirubin in blood is jaundice. Determination of the bilirubin content in blood has been an important item of clinical chemical testing.

Bilirubin is a yellow colorant which itself has an absorption peak at 435 nm or 465 nm and molecular absorptivity coefficient of about $5 \times 10^4$ $C_{33}H_{36}O_6N_4$.

Bilirubin can be detected by examining the density of green color formed when bilirubin is oxidized by an oxidizer to biliverdin and by knowing precisely how this density is proportional to bilirubin content. This method is associated with qualitative testing. Disadvantages with this method is that it can be difficult to quantitate the amount of bilirubin in a sample.

Various calorimetric methods for determining bilirubin concentration have been proposed. In one method, bilirubin is coupled with a diazonium salt such as diazosulfanilic acid and the amount of the resulting colorant is measured in a spectrophotometer to estimate the bilirubin content. However, since the bilirubin content in the blood serum of a healthy subject is very small, it can be difficult to achieve accurate determination of the bilirubin concentration using this method. bilirubin is extracted from an aqueous solution with a hydrophobic organic solvent. A disadvantage with this method is that it can take time to extract the bilirubin from an aqueous solution and it can require large amounts of sample which can be difficult to concentrate, which can lead to low extraction recovery. A further disadvantage associated with this method is that this method may not be specific for measuring the conjugated species of bilirubin.

For the foregoing reasons, there is a need for a sensitive specific assay that can accurately determine the presence of an analyte in a sample that undergoes auto-oxidation. Further, it would be advantageous to have an assay which would be capable of satisfying the above criteria yet able to maintain the standardization of the assay by avoiding auto-oxidation.

SUMMARY

The present invention is directed to an assay that meets these needs. The assay is used to detect in a test sample an analyte that undergoes auto-oxidation. The assay comprises the steps of forming a reaction mixture by combining in an aqueous medium (i) a sample containing the analyte and (ii) a stabilizer that reduces the rate of radical mediated auto-oxidation of the analyte. The reaction mixture is then incubated for a period of time and the rate of auto-oxidation can be detected.

When the detected rate of auto-oxidation is substantially zero, a sufficient quantity of an enzyme that catalyzes the oxidation of the analyte, can be added to the reaction mixture. In the presence of the stabilizer, the analyte can be oxidized to a product species. The product species, the analyte, or both can be detected.

This assay can be performed on test samples such as serum, plasma, saliva, pleural or cerebral spinal fluid, amniotic fluid, urine, feces, mucus, cell extracts, tissue extracts and pus.

The stabilizer can be a free radical scavenger such as mannitol, inositol, tocopherol, superoxide dismutase, catalase, glutathione, glutathione peroxidase, 2-mercaptoethanol, N-2-mercapto propenyl glycine, dimethyl urea, dimethyl thiourea, butylated hydroxytoluene, butylated hydroxyanisole, the 21-aminosteroids, deferoxamine, allopurinol, dimethyl sulfoxide and coenzyme Q.

Typically, the concentration of the scavenger can be used from about 5 mM to about 150 mM. Preferably, the concentration of the scavenger is from about 30 mM to about 100 mM.

Preferably, the free radical scavenger is mannitol. When the free radical scavenger is mannitol, the concentration of mannitol preferably is 50 mM.

The aqueous medium comprises a buffered aqueous solution having a pH which can substantially provide a medium for obtaining a sufficiently high reaction rate for the enzyme, whereby the enzyme has substantially high specificity towards the analyte of interest. Preferably, the buffered aqueous solution is capable of maintaining the pH at an alkaline pH. More preferably, the buffered aqueous solution is glycine buffer.

The reaction mixture can further comprise chelators for removing undesirable metal ions from the medium. The chelators can be selected from the group consisting of ethylene diamine tetra acetic acid, ethylene glycol bis(beta-aminoethyl ether)-N,N,N',N'-tetraacetate and 2,2-bis (hydroxyethyl)-2,2',2"-nitrolotriethanol.

The analyte can be selected from the group consisting of bilirubin, glucose, cholesterol, neutral fats, free fatty acids, phospholipids and uric acids. Preferably, the analyte is bilirubin.

The enzyme can be selected from the group consisting of bilirubin oxidase, glucose oxidase, cholesterol oxidase, uricase, acyl coenzyme A oxidase, choline oxidase, and glycerol-3-phosphate oxidase. Preferably, the analyte is bilirubin, and the product species is biliverdin.

The assay can be used to detect in a test sample an analyte, such as bilirubin, that undergoes auto-oxidation. The assay comprises the steps of forming a reaction mixture by combining in an aqueous medium (i) a sample containing the bilirubin and (ii) a mannitol as a stabilizer that reduces the rate of radical mediated auto-oxidation of bilirubin. The reaction mixture is then incubated for a period of time and the rate of auto-oxidation can be detected.

When the detected rate of auto-oxidation is substantially zero, a sufficient quantity of an bilirubin oxidase can be added, that catalyzes the oxidation of the bilirubin, which in the presence of the mannitol, bilirubin can be oxidized to the product biliverdin. Biliverdin, bilirubin, or both can be detected.

DESCRIPTION OF THE DRAWINGS

These and other features, aspects, and advantages of the present invention will become better understood with reference to the following description and appended claims, and accompanying drawings where:

DESCRIPTION

Figure 1:
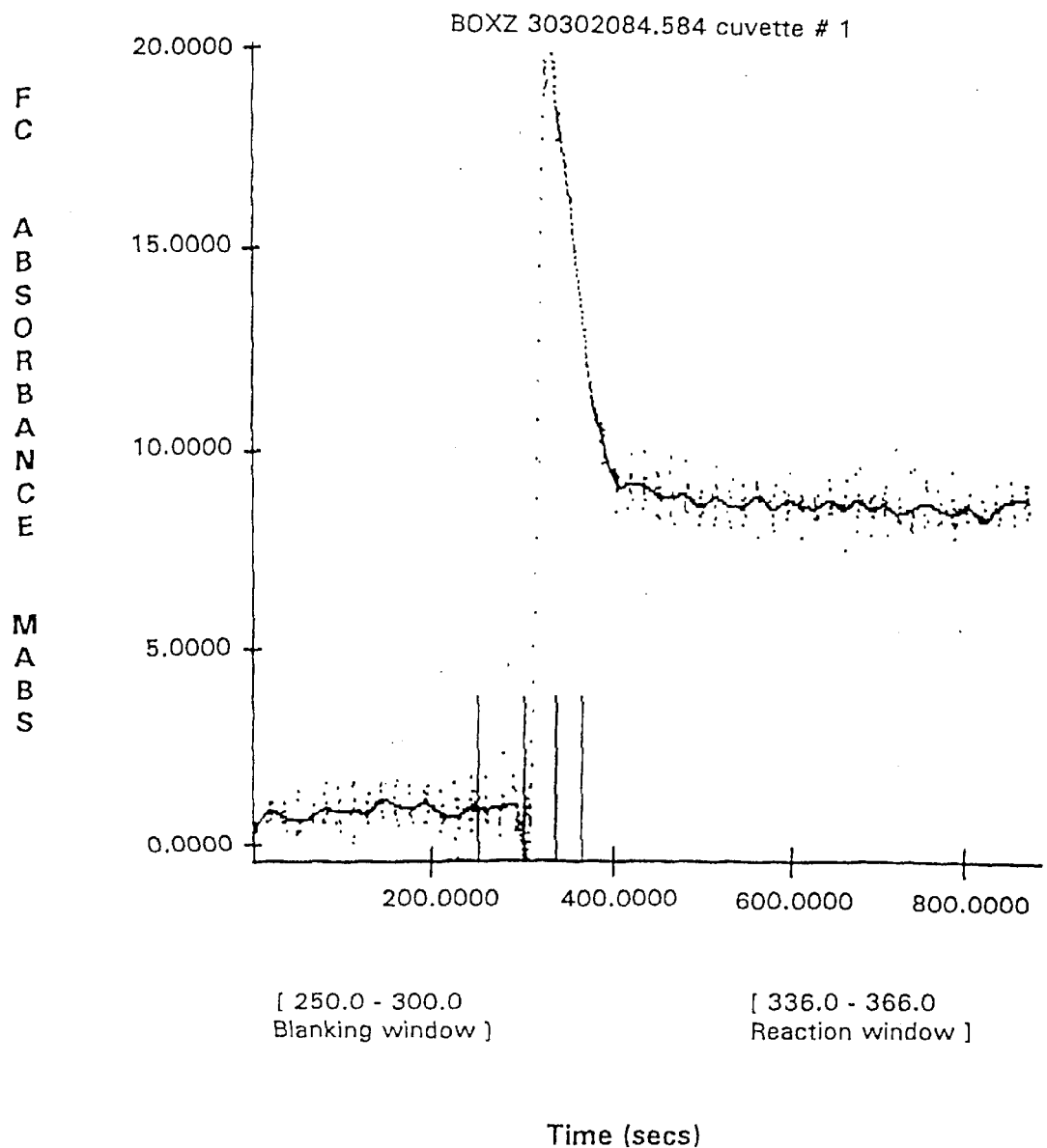
FIG. 1 is a graph showing a typical reaction curve for testing bilirubin using the bilirubin oxidase method on a Synchron CX5 Analyzer.

According to the present invention, there is a provided an assay for detecting in a test sample, an analyte of interest that undergoes auto-oxidation. Such an assay comprises the steps of forming a reaction mixture, incubating the reaction mixture, adding to the mixture a sufficient quantity of enzyme to the reaction mixture and detecting the product species, the presence of the analyte in the test sample or both.

I. FORMING THE REACTION MIXTURE

The reaction mixture is formed by combining in an aqueous medium, (i) a sample containing the analyte and (ii) a stabilizer that reduces the rate of radical mediated auto-oxidation of the analyte.

A. The Aqueous Medium

The aqueous medium can any suitable liquid, such as water, which is capable of acting as a solvent for all the components of the reaction mixture at their desired concentrations. Typically, the aqueous medium comprises a buffered aqueous solution having a pH which can substantially provide a medium for obtaining a sufficiently high maximum reaction rate for the enzyme, whereby the enzyme has substantially high specificity towards the analyte of interest. Preferably, when bilirubin oxidase is the enzyme used to measure the oxidation of conjugated bilirubin, the buffered aqueous solution is between about pH 8 to about pH 10.

Specifically, with measuring bilirubin, at low pH's, hemoglobin can convert rapidly to ferriheme in the diazo method, which can result in a high yield of $H_2O_2$ which can interfere with the assay. Additionally, at acidic pH, enzymatic methods measure all direct reacting bilirubins, while at pH 10, only conjugated bilirubins are measured. The measurement of conjugated bilirubins can be more helpful than the measurement of direct bilirubin in the differential diagnosis of jaundice. Typically, the buffer can be a buffer like TRIS. More preferably, the buffered aqueous solution is glycine buffer, because glycine buffer can provide a stable strong buffering capacity at reaction pH 10 which can provide a medium for obtaining a sufficiently high maximum reaction rate for bilirubin oxidase (BOX), whereby bilirubin oxidase has substantially high specificity towards bilirubin. In alkaline buffer with pH around 10, bilirubin oxidase can specifically oxidize the conjugated bilirubin (Bc; mono and diglucuronides) to biliverdin. This oxidative reaction can be monitored at wavelength of 460 nm. Typically, the resulting decrease in absorbance is linearly related to the concentration of Bc in the test sample.

Preferably, the reaction mixture comprises a glycine buffer which has a low absorbance at the typical measurement wavelengths of from about 300 nm to about 700 nm typically used in assays to measure catalytic activity.

Additionally, the assay medium can include reagents which do not interfere with the oxidation process of the analyte such as surfactants such as Triton X-100 and Tween-20.

1. The Test Sample

The test sample preferably contains an analyte of interest that undergoes auto-oxidation. The test sample can be any biological fluid including serum, plasma, saliva, pleural or cerebral spinal fluid, amniotic fluid, urine, feces, mucus, cell extracts, tissue extracts and pus.

The analyte of interest is a substance suspected of being in the test sample whose presence or concentration is to be determined. The analyte of interest is most preferably a material that undergoes auto-oxidation and is typically bilirubin, glucose, cholesterol, neutral fats, free fatty acids, phospholipids and uric acids. More preferably, the analyte is bilirubin and this bilirubin is in its conjugated state. Bilirubin is inherently not present in the free state in biological fluids, but present in the form of either conjugated bilirubin (bilirubin combined with glucuronic acid, sulfuric acid, hydrochloric acid or the like) or unconjugated bilirubin (bilirubin combined with albumin). It is believed that conjugated bilirubin increases in cases of liver cell lesion, hepatic jaundice, and posthepatic jaundice, whereas unconjugated bilirubin increases in the cases of liver dysfunction. Measuring the conjugate state of bilirubin can be a sensitive specific indicator for hepatic disease as compared to measuring direct bilirubin.

2. Stabilizer

The stabilizer present in the aqueous medium can be any substance capable of reducing the rate of radical mediated auto-oxidation of the analyte. Further, the stabilizer can be capable of reducing the rate of radical mediate auto-oxidation of any other substance present in the aqueous medium that could interfere with the assay. A variety of free radical scavengers, such as for example, mannitol, inositol, tocopherol, superoxide dismutase, catalase, glutathione, glutathione peroxidase, 2-mercaptoethanol, N-2-mercapto propenyl glycine, dimethyl urea, dimethyl thiourea, butylated hydroxytoluene, butylated hydroxyanisole, the 21-aminosteroids, deferoxamine, allopurinol, dimethyl sulfoxide and coenzyme Q, can be used as a the stabilizer. Preferably, the free radical scavenger is mannitol.

The free radical scavenger stabilizer can be used at a concentration from about 5 mM (millimoles per liter) to about 150 nM in the aqueous medium. Less than about 5 mM of the free radical scavenger in the aqueous medium may not be able to provide enough free radical scavenger to stabilize a significant amount of the analyte that undergoes auto-oxidation. More than about 150 mM of the free radical scavenger in the aqueous medium can be difficult to solubilize the solution. Preferably, the stabilizer is used in a concentration from about 30 mM to about 100 mM which can be an effective stabilizer concentration range. More preferably, when mannitol is used as the stabilizer, the concentration of mannitol is 50 mM.

Typically, the assay is used to measure the analyte of interest through a spectrophotometric light absorption method. When a spectrophotometric assay method is used, it is important that the scavenger is substantially transparent to light at the measurement wavelength to not interfere with the light absorption measurements used to detect catalytic activity of the assay.

3. Chelators

Forming the reaction mixture can further include the addition of chelators for removing undesirable metal ions from the reaction mixture, such as $Fe^{+2}$, which if present, can affect the catalytic activity of the enzyme. Auto-oxidation of the analyte of interest can be enhanced by the presence of transition metal ions such as $Fe^{+2}$ and $Cu^{+2}$. Auto-oxidation can be mediated through an oxygen radical propagation. Metal ion chelators may be able to diminish auto-oxidation of the analyte and the absorbance drift of sample blanking.

The amount of chelator added to an assay depends on the assay in question. This amount can be determined for each assay by determining what metal ions are present in the assay. Typically, the amount of chelator added to the reaction mixture is an amount that can substantially remove undesirable metal ions from the reaction mixture and does not interfere with the assay.

Preferably, chelators such as ethylene diamine tetra acetic acid (EDTA), ethylene glycol bis(beta-aminoethyl ether)-N,N,N',N'-tetraacetate (EGTA) and 2,2-bis(hydroxyethyl)-2,2',2''-nitrolotriethanol (BHN) can be used to remove multivalent cations, such as $Fe^{+2}$ from the reaction mixture.

If the reaction mixture does not contain any iron ions, then the need for a chelator in the reaction mixture is significantly reduced. A constraint on the amount of the chelator used is to avoid having an amount of chelator present such that the chelation of excessive amounts of useful metal ions present in the reaction mixture can occur.

When the analyte of interest is bilirubin, a chelator such as EDTA, EGTA or BHN can be added to the reaction mixture. The chelator is-preferably used in a concentration of from about 0.025 mmol/L to about 4 mmol/L. Less than about 0.025 mmol/L of chelator in the reaction mixture does not provide enough chelator to remove a significant amount of undesired metal ions which may be present in the reaction mixture. More than about 4 mmol/L of chelator can result in chelation of excessive amounts of useful metal ions. More preferably, the chelator is present in the reaction mixture in a concentration of from about 0.5 mmol/L to about 2 mmol/L.

II. INCUBATING THE REACTION MIXTURE AND DETECTING THE RATE OF AUTO-OXIDATION

In the incubating step, the reaction mixture incubates for a period of time and the rate of auto-oxidation of the analyte is detected. Typically, this is done spectrophotometrically.

III. ADDING TO THE REACTION MIXTURE

When the rate of auto-oxidation of the analyte is substantially zero, a sufficient quantity of an enzyme that catalyzes the oxidation of the analyte is added. In the presence of the stabilizer, the analyte is oxidized to a product species.

1. Enzyme

Frequently, conventional methods for the quantitative determination of analytes of interest in biological fluids can use oxidizing enzymes.

Typically, the enzyme can be any enzyme capable of oxidizing an analyte of interest. Preferably, the enzyme is selected from the group consisting of bilirubin oxidase, glucose oxidase, cholesterol oxidase, uricase, acyl coenzyme A oxidase, choline oxidase, and glycerol-3-phosphate oxidase.

More preferably, the enzyme is bilirubin oxidase (BOX) and is selected from the group consisting of Myrothecium sp. bilirubin oxidase and coprinus sp. bilirubin oxidase.

Bilirubin oxidase can be used to measure bilirubin by oxidizing bilirubin to biliverdin. The enzyme can be characterized by no formation of hydrogen peroxide in the course of oxidation. The enzymological properties of bilirubin oxidase include: BOX is stable between pH 9.2 to 9.7 for 5 days at 40° C. and has a pH range from 6–10. BOX can be inhibited by $Fe^{+2}$, and KCN (potassium thiocyanate) and partially inhibited by sodium azide, thiourea or sodium chloride.

BOX can catalyze the oxidation of bilirubin to biliverdin by molecular oxygen without the formation of hydrogen peroxide.

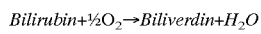

$$Bilirubin + \tfrac{1}{2}O_2 \rightarrow Biliverdin + H_2O$$

The oxidation rates for various bilirubin fractions can depend on the pH of the reaction mixture and on the presence of surfactants. Conjugated bilirubins can be rapidly oxidized over a wide range of pH's, showing maxima near pH values 4.5 and 10.0. At low pH (3.7 to 4.5), BOX can oxidize bilirubin conjugates and most of delta bilirubin to biliverdin. Unconjugated bilirubin is not oxidized. At pH 10, BOX can oxidize bilirubin conjugates, but not the unconjugated or delta bilirubins, to biliverdin. At either pH the reaction can proceed in the absence of surfactants, and the decrease in absorbance near 460 nm can be proportional to the concentration of direct bilirubin.

The amount of enzyme used for the determination of bilirubin preferably is such that the concentration of bilirubin in the reaction mixture is equal to 0.003 to about 0.40 U/mL of bilirubin oxidase. The unit of bilirubin oxidase activity is defined as follows: Five mg of bilirubin crystals are dissolved in 250 ml of a 0.2M tris-HCl buffer solution (pH 8.4) containing 1 mM EDTA. A 2-ml portion of the resulting solution is mixed with 0.2 ml of enzyme solution. The mixture is incubated at 37° C. and its absorbance decrease at 440 nm is then measured. Thus, the amount of enzyme which oxidizes 1 micromole of bilirubin per minute is defined as one unit.

IV. DETECTING THE PRODUCT SPECIES, ANALYTE OR BOTH

In the detection step, the product species, analyte or both can be measured. Typically, the assay is carried out using a spectrophotometer to measure the change in light absorption. Typically, a wavelength of less than about 600 to 700 nm (nanometers), such as 460 nanometers is used to spectrophotometrically measure the light. Preferably, the oxidative reaction is monitored at wavelength of 460 nm due to the specific oxidation of conjugated bilirubin by bilirubin oxidase resulting in a decrease in absorption.

V. TEST KIT

Formulations for use in assays to detect the analyte of interest can be assembled as test kits of at least one or more containers. These test kits can provide a convenient assortment of stable assay components which can be partially or completely precombined or uncombined.

In the interest of clarity, the following example is intended to illustrate, but in no way limit the scope of, the present invention.

EXAMPLE (Prospective)

Assays can be carried out using a SYNCHRON Clinical Chemistry Autoanalyzer (CX4, CX5, CX4CE, CX5 CE, CX7 and LX), Beckman Instruments, Inc. (Fullerton, Calif.).

The optical absorbance readings of the reaction mixture can be measured at 465 nm using a DU®-7600 Spectrophotometer (Beckman Instruments).

Bilirubin quantitation by the bilirubin oxidase method (BOX) can be carried out.

The glycine buffer can be prepared to contain the following:

Component A: Reaction Buffer
- 0.1 Glycine (Sigma Chemical Co. (St. Louis, Mo.), P/N G-7126)
- 0.05M Mannitol (Sigma Chemical Co. (St. Louis, Mo.), P/N M-9647)
- 0.005 M EDTA (Sigma Chemical Co. (St. Louis, Mo.), P/N E-9884)

Component C: Bilirubin Oxidase (BOX) (Trigger)
- 75 U/mL BOX (Beckman Dri-Stat, P/N 683802)
- 0.01M Glycine (Sigma Chemical Co. (St. Louis, Mo.), P/N G-7126)
- 0.05 Mannitol (Sigma Chemical Co. (St. Louis, Mo.), P/N M-9647)

Concentration range of mannitol: 5–100 mM.

General Assay Procedures (SYNCHRON CX4/5/7 Autoanalyzer): (See FIG. 1)

-320 second: Reaction Buffer (A) Injection, 220 uL 0 second: Sample Injection, 7 uL 16 second: BOX Trigger (C), 14 uL (equivalent to 1U per assay)

Blank window: 250–300 seconds

Reaction Window: 336–366 seconds

The time of sample addition is set as "zero seconds" of the entire assay time scale. The time prior to the sample addition is denoted as 320 seconds according to FIG. 1.

1. In a cuvette, add buffer and incubate at 37° C. for -320 seconds to equilibrate the temperature of the solution.
2. Add sample and incubate for a period of time (30–90 seconds), and calculate sample blanking rate of absorbance change during this period.
3. Add bilirubin oxidase enzyme (BOX) solution to carry out the enzymatic reaction for seconds.
4. Calculate sample reaction rate in absorbance change during this period.
5. Net reaction rate=sample reaction—sample blanking
6. Algorithm:

Since the bilirubin concentration in sample is proportional to its net reaction rate, a linear calibration curve can be constructed with two calibrators of known bilirubin concentrations, and bilirubin concentration in the sample can be calculated from the equation (Y=ax+b) of the calibration curve.

The following results show the prevention of bilirubin auto-oxidation by 50 mM mannitol in glycine buffer (0.1M, pH 10.5)

|  | Drift rate (mA/min) | |
| --- | --- | --- |
|  | 0~100 sec. | 100~300 sec. |
| Glycine Buffer | −2.70 | −1.20 |
| Glycine Buffer + 50 mM mannitol | −1.02 | −0.15* |

*This drifting rate is insignificant and buried in the instrument noise

The previously described versions of the present invention have many advantages. The advantages include having an assay which can detect an analyte of interest that undergoes auto-oxidation in a test sample. Specifically, with respect to the measurement of BOX catalyzed oxidation of bilirubin, this assay can provide an accurate a precise chemical reaction assay with a short reaction time (approximately five minutes) and furthermore, allows this assay to be more applicable to random access autoanalyzers without affecting the instrument throughput.

Although the present invention has been described in considerable detail with reference to certain preferred versions, other versions are possible. Thus the spirit and scope of the appended claims should not be limited to the description of the preferred versions contained herein.

What is claimed is:

1. A test kit for detecting in a test sample, an analyte that undergoes auto-oxidation, the test kit including at least one container containing the following components which are partially or completely precombined or uncombined, the test kit comprising:
   (a) an aqueous medium;
   (b) a stabilizer that reduces the rate of radical mediated auto-oxidation of the analyte, wherein when the stabilizer is a free radical scavenger, the concentration of the stabilizer is from about 5 mM to about 150 mM; and
   (c) a quantity of an enzyme sufficient to catalyze oxidation of the analyte to a product species, wherein the quantity of enzyme is added to the reaction mixture when the rate of auto-oxidation of the analyte is substantially zero.

2. The test kit of claim 1, wherein the test sample is selected from the group consisting of serum, plasma, saliva, pleural or cerebral spinal fluid, amniotic fluid, urine, feces, mucus, cell extracts, tissue extracts and pus.

3. The test kit of claim 1, wherein the free radical scavenger is selected from the group consisting of mannitol, inositol, tocopherol, superoxide dismutase, catalase, glutathione, glutathione peroxidase, 2-mercaptoethanol, N-2-mercapto propenyl glycine, dimethyl urea, dimethyl thiourea, butylated hydroxytoluene, butylated hydroxyanisole, the 21-aminosteroids, deferoxamine, allopurinol, dimethyl sulfoxide and coenzyme Q.

4. The test kit of claim 3, wherein the free radical scavenger is mannitol.

5. The test kit of claim 3, wherein the concentration of the scavenger is from about 30 mM to about 100 mM.

6. The test kit of claim 3, wherein the concentration of mannitol is 50 mM.

7. The test kit of claim 1, wherein the aqueous medium comprises a buffered aqueous solution having a pH which can substantially provides a medium for obtaining a sufficiently high maximum reaction rate for the enzyme, whereby the enzyme has substantially high specificity towards the analyte.

8. The test kit of claim 1, wherein the analyte is selected from the group consisting of bilirubin, glucose, cholesterol, neutral fats, free fatty acids, phospholipids and uric acids.

9. The test kit of claim 8, wherein the analyte is bilirubin.

10. The test kit of claim 9, wherein the bilirubin is conjugated.

11. The test kit of claim 1, wherein the enzyme is selected from the group consisting of bilirubin oxidase, glucose oxidase, cholesterol oxidase, uricase, acyl coenzyme A oxidase, choline oxidase, and glycerol-3-phosphate oxidase.

12. The test kit of claim 1, wherein the enzyme is bilirubin oxidase and is selected from the group consisting of Myrothecium sp. bilirubin oxidase and coprinus sp. bilirubin oxidase.

13. The test kit of claim 1, wherein when the analyte is bilirubin, and the product species is biliverdin.

* * * * *